United States Patent [19]

Cullor

[11] Patent Number: 4,987,079

[45] Date of Patent: Jan. 22, 1991

[54] COMPOSITION AND METHOD FOR IN VITRO CELL CULTURE

[75] Inventor: James S. Cullor, 128 Shasta Pl., Woodland, Calif. 95615

[73] Assignees: Wilbur D. Smith; James Cullor; James S. Cullor; Gary W. Cullor, Fort Scott, Kans.

[21] Appl. No.: 390,453

[22] Filed: Aug. 4, 1989

Related U.S. Application Data

[63] Continuation of Ser. No. 782,600, Sep. 30, 1985, abandoned, which is a continuation of Ser. No. 480,355, Mar. 30, 1983, abandoned, which is a continuation-in-part of Ser. No. 395,830, Jul. 6, 1982, abandoned.

[51] Int. Cl.$^5$ .......................... C12N 5/00; C12N 5/06
[52] U.S. Cl. .............................. 435/240.2; 435/240.3; 435/240.31
[58] Field of Search ............... 435/240.2, 240.3, 240.31

[56] References Cited

U.S. PATENT DOCUMENTS

| | | | |
|---|---|---|---|
| 4,094,097 | 6/1978 | Alexander et al. | 435/245 X |
| 4,172,124 | 10/1979 | Koprowski et al. | 435/240 X |
| 4,276,282 | 6/1981 | Sugimoto et al. | 435/68 X |
| 4,350,683 | 9/1982 | Galfre et al. | 435/240 X |
| 4,377,513 | 3/1983 | Sugimoto et al. | 435/240 X |
| 4,420,563 | 12/1983 | Chen et al. | 435/245 |
| 4,472,500 | 9/1984 | Milstein et al. | 435/68 |

FOREIGN PATENT DOCUMENTS

| | | |
|---|---|---|
| 305264 | 4/1955 | Switzerland . |
| 2093038 | 8/1982 | United Kingdom . |

OTHER PUBLICATIONS

Price et al., Chem. Abst., vol. 97 (1982), p. 123, 408 Z.
Chang et al., "Human Amniotic Fuel Cells Grown in a Hormone-Supplemented Medium: Suitability for Prenatal Diagnosis", Medical Sciences Proceedings National Academy of Science USA, 79, Aug. 1982, pp. 4795-4799.
Reidy et al., "Reducing the Use of Fetal-Calf Serum in Culturing Amniotic-Fluid Cells", New England Journal of Medicine, 303 No. 12, Sep. 1980, pp. 704-705.
Calvert, "Effect of Amniotic Fluid and Fetal Bovine Serum on the Morphogenesis of Mouse Duodenal Villi in Organ Culture", Experientia, 37, 1981, pp. 417-418.
Parker, Methods of Tissue Culture, New York, Harper & Row, 1961, pp. 108-111.
Biological Abstracts, vol. 72, 1981, Abstract No. 84630, Kwon et al.

*Primary Examiner*—Sam Rosen
*Attorney, Agent, or Firm*—Hovey, Williams, Timmons & Collins

[57] ABSTRACT

An improved method and apparatus is disclosed for adding fluids to, or removing fluids from, a body part or organ of an animal which minimizes animal trauma and permits rapid, easy, repeated fluid or low viscosity gel transfers. The apparatus includes a tubular fluid-conveying element adapted for fixed connection to the animal, along with a flexible fluid conduit connected between the element and a specific internal body part or organ, such as a cow's uterus. In use, a syringe is employed to introduce or remove fluids from the body part, through the tubular element and connected conduit. The invention is especially adapted for introducing and recovering cell lines producing monoclonal antibodies or other biologically active products in large mammals, and fascilitates monitoring of antibody production as well as administration of nutrients to enhance cell line growth. In preferred monoclonal antibody production procedures, the cells are initially educated through in vitro contact with ambient fluid of the selected organ (e.g., allantoic fluid from a pregnant host and fetal calf serum), whereupon the educated cells are inoculated and allowed to incubate in the host. It has been found particularly advantageous to employ the allantois of a pregnant mammal for antibody production, and some or all of the cell incubation period therein should occur after the onset of immunocompetency of the fetus.

6 Claims, 4 Drawing Sheets

COMPOSITION AND METHOD FOR IN VITRO CELL CULTURE

This application is a continuation of application Ser. No. 782,600 filed Sept. 30, 1985; which was a continuation of application Ser. No. 480,355 filed Mar. 30, 1983; which was a continuation-in-part of application Ser. No. 395,830 filed July 6, 1982, all now abandoned.

BACKGROUND OF THE INVENTION

1. Field of the Invention

The present invention is broadly concerned with a method and apparatus designed to greatly facilitate addition of fluids to, or removal of fluids from, an internal body organ or part of an animal. More particularly, it is concerned with such a method and apparatus which is especially suited for the large scale production of monoclonal antibodies in large mammals, and which permits repeated monitoring and/or nutritional enhancement of the in vivo monoclonal antibody production procedure. In preferred methods, monoclonal antibody production is enhanced by in vitro education of the cells using fluid characteristic of the host organ; moreover, use of the allantois of a pregnant host (e.g., cow, horse, sheep or pig) after the onset of fetus immunocompetency is especially advantageous.

2. Description of the Prior Art

When a foreign substance enters the body of a vertebrate animal or is injected into it, one aspect of the immune response is the secretion by plasma cells of antibodies. Quite apart from the natural function of antibodies in the animal's immune response, such antibodies have long been an important tool for investigators, who capitalize on their specificity to identify or label particular molecules or cells and to separate them from a mixture. The antibody response to a typical antigen is normally highly heterogeneous, and even the best of antisera are really heterogeneous mixtures of many different antibody molecules that vary in charge, size, and in such biologic properties as the ability to fix complement or to agglutinate or precipitate antigen. It is extremely difficult to separate the various antibodies in antisera, and therefore conventional antisera contain mixtures of antibodies, and such mixtures vary from animal to animal.

It is also known that malignant tumors of the immune system (called myelomas) are characterized by rapidly proliferating cells producing large amount of abnormal immunoglobulines called myeloma proteins. A tumor itself is considered to be an immortal clone of cells descended from a single progenitor, and so myeloma cells can be cultured indefinitely, and all the immunoglobulins they secrete are identical in chemical structure. They are in effect monoclonal antibodies, but there is no way to know what antigen they are directed against, nor can one induce myelomas that produce antibody to a specific antigen. However, in recent years researchers have learned how to fuse myeloma cells of mice with lymphocytes from the spleen of mice immunized with a particular antigen. The resulting hybrid-myeloma, or "hybridoma" cells express both the lymphocyte's property of specific antibody production and the immortal character of the myeloma cells. Such hybrid cells can be manipulated by the techniques applicable to animal cells in permanent culture. Individual hybrid cells can be cloned, and each clone produces large amounts of identical antibody to the single antigenic determinant. The individual clones can be maintained indefinitely, and at any time samples can be grown in culture or injected into animals for large scale production of monoclonal antibody. Highly specific monoclonal antibodies produced by this general method have proved to be a versatile tool in many areas of biological research and clinical medicine.

While the utility of specific monoclonal antibodies is manifest, a problem has arisen because of the difficulty of producing significant (e.g., liter) quantities of the antibodies. Obviously, the production of such antibodies in mice is not at all suited for large scale production.

In response to this problem, it has been suggested to employ large mammals such as cattle or sheep for in vivo production of monoclonal antibodies. In one such procedure, the cells of hybridoma clones are introduced into the amniotic fluid of a cow in the early stages of gestation prior to the onset of fetal immunocompetency and are allowed to multiply. After a suitable growth period, quantities of monoclonal antibodies can be harvested. While the above described technique shows considerable promise, a number of practical problems remain. For example, it is desirable to monitor the production of monoclonal antibodies during incubation thereof, and the problems of obtaining samples of the amniotic fluid on a frequent recurrent basis are formidable. The straightforward procedure of simply making a laparotomy incision in the cow's body, manipulation of the uterus, introducing or withdrawing materials, can create multiple insults to the cow, uterus and fetus, which may lead to premature death, infection, or abortion of the fetus. By the same token, in order to enhance antibody production in the amniotic fluid, it is oftentimes desirable to introduce nutrient fluids into the uterus. Here again, the conventional techniques for such introduction, if used repeatedly, can cause severe problems to the animal and uterine environment.

Prior art patents describing various types of percutaneous transport tubes and related structure include: U.S. Pat. Nos. 4,315,513, 3,401,689, 3,515,124, 3,570,484, 3,583,387, 3,961,632 and 3,333,588. All of the structures described in the aforementioned patents are deficient in important respects, and would present serious problems if it were attempted to use the same in the context of in vivo monoclonal antibody production.

In addition, the prior practice of simply placing a cell line in amniotic fluid often leads to rapid death of a large proportion of cells. That is to say, cell lines of interest are typically cultured in highly specific and optimized media, and under relative critical conditions. For example, many cell lines are cultured and allowed to multiply at incubation temperatures of 37 degrees centigrade in specially prepared media, with periodic screening and feeding at regular intervals (e.g., every 48-72 hours). Prior to inoculation, the cells are concentrated into a fixed volume of their media plus fetal calf serum and are surgically implanted. However, this procedure gives only mediocre results, and can often fail completely in that the cells do not multiply or do not produce the desired antibody. One problem with this approach is that the cells, when inoculated, can experience severe "shock" owing to the radically different ambient environment of the amniotic fluid as compared with the previous in vitro culture media and scrupulously maintained growth conditions.

Finally, use of amnionic fluid of a pregnant host as a growth media for hybridoma cells leads to a number of additional difficulties. Specifically, in the case of cattle, it is known during the second trimester of gestation the amnionic fluid consistency changes and it becomes gel-like. Moreover, the fetus swallows substantial quantities of the amniotic fluid, especially during the first trimester of gestation. For the foregoing reasons, prior in vivo attempts to produce monoclonal antibodies using amnionic fluid have been conducted during early stages of gestation so that the entire procedure is accomplished prior to the onset of fetal immunocompetency. If the procedure is carried on after the fetus becomes immunocompetent, the fetus will treat the inoculated cells as antigens and will develop appropriate antibodies, thereby killing the cells. Accordingly, the gestational time frame for cell growth is severely limited and critical in the case of amnionic fluid. Also, surgical manipulation of the fetus and amnionic sac during the early stages of pregnancy is difficult (because of uterine anatomical positioning, flank incisions, high paralumbar fossa, must be utilized), and this can lead to spontaneous abortion and/or fetal infection. Thus, while use of the amnionic fluid of a pregnant host is theoretically possible, a number of practical problems remain.

It will therefore be seen that there is a real and unsatisfied need in the art for methods and apparatus which permit easy, rapid addition to fluids to, or removal of fluids from, specific body parts or organs of animals, so as to facilitate the production and monitoring of monoclonal antibodies, while at the same time avoiding repeated insults to the animal and other internal organs and problems of unintended cell death and low levels of antibody production.

SUMMARY OF THE INVENTION

The foregoing problems are in large measure solved by the present invention which provides, in one aspect, a greatly improved method and apparatus especially adapted for the large scale cell growth in living mammals, such as in the production of monoclonal antibodies. Broadly speaking, the apparatus is designed for selectively withdrawing fluids from, or adding fluids to, an animal's body, and includes an assembly including a tubular, fluid-conveying element designed to be coupled to the animal's body with the outer end of the element being adjacent the exterior surface of animal's skin. An elongated, flexible, fluid-conveying conduit having an inner end and an outer end also forms a part of the apparatus; the outer end of the conduit is operably coupled and in fluid flow communication with the tubular element, whereas the inner conduit end is configured for insertion through the wall of a specific organ or the like of the living animal, with the innermost portion of the flexible conduit lying within the organ. The conduit is advantageously of a length greater than the shortest distance between the element and the point of insertion thereof through the wall of the organ so that the conduit permits and accommodates natural movement of the organ over time. Finally, the overall apparatus includes means for physically attaching and interlocking the inner end of the conduit to the organ wall so as to prevent leakage of fluid from the organ.

In preferred forms, the overall fluid-conveying element includes selectively operable valve means which minimizes the risk of infection of the host animal; however, such valve apparatus is not absolutely essential.

In other forms of the apparatus, the innermost portion of the conduit is of a larger diameter than the remaining portion of the conduit, and is formed of a soft, flexible material such as silicone rubber.

In the use of the preferred apparatus of the invention, the fluid-conveying element is secured to the animal's body with the outer end of the element adjacent the exterior surface of the animal's skin, and the fluid conduit is coupled to the element and a selected organ such as a uterus. The coupling step involves making an incision in the wall of the selected organ and inserting the inner end of the conduit into the organ. The conduit is physically attached and interlocked to the wall of the organ, as by suturing an appropriate collar affixed to the conduit, so that leakage from the organ is prevented. Once the apparatus is installed, fluid can be periodically and selectively withdrawn from, or added to, the organ, as by use of a conventional syringe or the like.

In other aspects of the invention, it has been found particularly advantageous to "educate" cells prior to inoculation thereof into the host organ. Such education generally includes contacting the cells with ambient fluid characteristic of the selected host organ or the like, on an in vitro basis. Typically, the cells are repeatedly contacted with respective quantities of the ambient fluid over a period of time, with the concentration of the ambient fluid being increased. In the case of bovine allantoic fluid, the initial contact would be with a fluid containing from about 5 to 10 percent by volume of the allantoic fluid, followed by step-wise contacting of the cells with additional fluid samples containing increasing concentrations of the allantoic fluid. During this education procedure, the cells become acclimated to the allantoic fluid and begin to multiply therein.

It has also been found that an improved method for cell growth can be provided by inoculating cells into the allantois of a pregnant host, particularly an animal selected from the group consisting of sheep, horses, pigs and cows. The cells are caused to multiply in the allantois of the host over a period of time, with at least a portion of the time period being after the onset of immunocompetency of the host's fetus. In particularly preferred forms, the entire procedure occurs after the onset of fetus immunocompetency, typically during the second and third trimesters of gestation. The final step involves harvesting the cells or the secretory products thereof, e.g., monoclonal antibodies.

DESCRIPTION OF THE PREFERRED EMBODIMENTS

Turning now to the drawings, and particularly FIGS. 1-6, conveying apparatus 10 in accordance with the invention is illustrated. Broadly speaking, the apparatus 10 includes a valve assembly 12 along with an elongated conduit 14. The valve assembly 12 in turn includes an elongated, tubular, fluid-conveying element 16, as well as valving means 18 carried within the element 16.

In more detail, the valve assembly 12 preferably includes an elongated, slightly tapered, open ended outer tubular component 20 formed of an appropriate synthetic resin material and having an outwardly extending screw thread 22 formed thereon. The upper end of the component 20 is provided with an enlarged flange-type head 24 having a plurality of circumferentially spaced apertures 26 therethrough, as well as an upstanding, central, threaded annular connector 28. An outermost, rounded, removable synthetic resin cap 30 is threaded onto connector 28 as illustrated, and includes an O-ring seal 32 which abuts the upper surface of head 24 (see FIG. 1). The component 20 is configured to present a continuous, stepped, internal bore 34 along the length thereof and has an internal O-ring seal 36 spaced downwardly from head 24.

The tubular element 16 is situated within the upper, enlarged diameter portion of bore 34, and includes a synthetic resin tubular member 38 which is threaded at its upper end, the latter extending to a point adjacent surrounding connector 28. The inner age 40, and is configured to present an annular, obliquely oriented engagement surface 42 which is important for purposes to be made clear. Another seal 44 is disposed about the upper end of the member 38, and is situated within the upper end of bore 34 (see FIG. 2).

Figure 2:
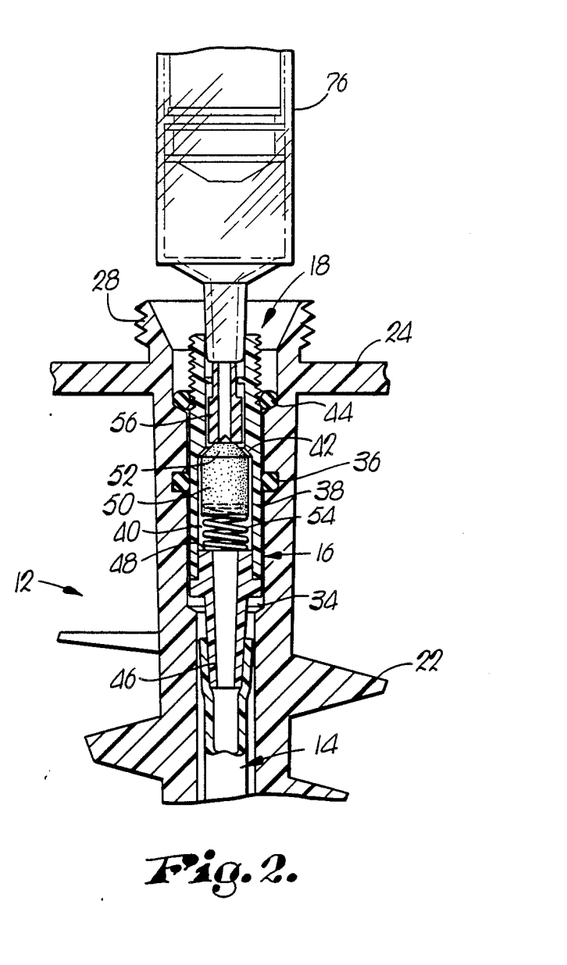
FIG. 2 is an enlarged, fragmentary view in partial vertical section illustrating the valve assembly of the FIG. 1 apparatus, with a syringe positioned for operating the internal valve means thereof.

The tubular element 16 also includes a lowermost tubular part 46 which is received within the lower end of member 38 and presents an annular abutment surface 48. The lower end of part 46 is of frustoconical configuration as best seen in FIG. 2. In addition, it will be observed that the bore of part 46 is coaxial and in communication with the passage 40 of member 38.

Valving means 18 is situated to normally block flow of fluid through the element 16. In detail, the valving means 18 includes a shiftable plug 50 presenting a conical upper sealing surface 52 which is complemental with and adjacent engagement surface 42 of member 38. A helical spring 54 is situated between the underside of plug 50 and the abutment surface 48, and serves to bias plug 50 against engagement surface 42 for purposes of normally sealing the member 38, and thus overall tubular element 16, against fluid flow therethrough.

A tubular actuator 56 is positioned atop plug 52 and in engagement with the latter. The actuator 56 extends upwardly from the plug 50 and into the annular region defined by the threaded upper end of the member 38. It will be observed in this respect that the actuator 56 is centrally bored for passage of fluids.

Figure 1:
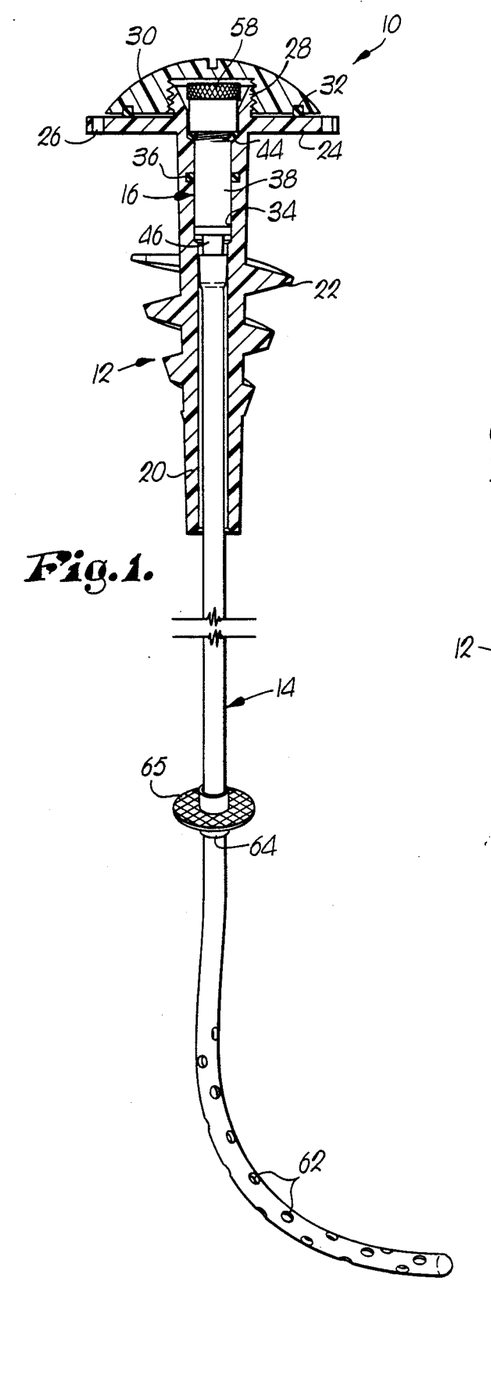
FIG. 1 is a fragmentary view in partial vertical section illustrating one embodiment of a fluid-conveying apparatus in accordance with the present invention.
Figures 3, 4, 5, 6:
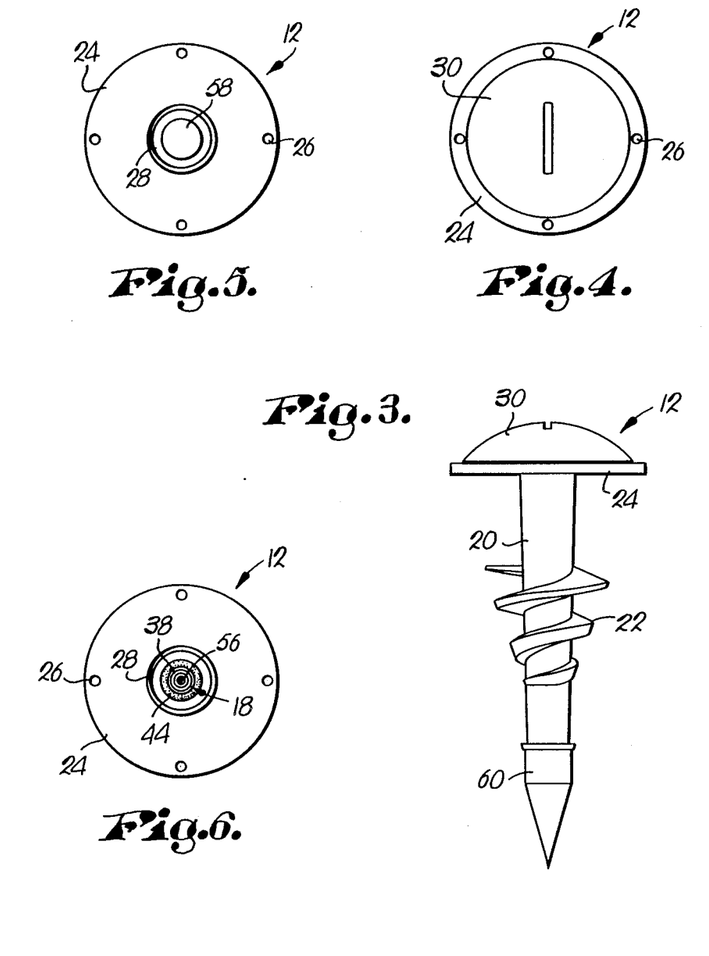
FIG. 3 is a side elevational view of the valve assembly prior to application thereof to an animal.
FIG. 4 is a top view of the assembly depicted in FIG. 3.
FIG. 5 is a top view, with the uppermost protective cap removed, of the assembly illustrated in FIG. 3.
FIG. 6 is a view similar to that of FIG. 5, but illustrates the inner protective cap removed to expose the internal valve means.

Referring to FIGS. 1 and 5, it will be seen that an inner cap 58 is advantageously applied to the upper threaded end of member 38, in order to further seal the internal valving means 18 when the latter is not in use. In addition (see FIG. 3), a removable insertion tip 60 is affixed to the lower open end of the tubular component 20.

Figure 7:
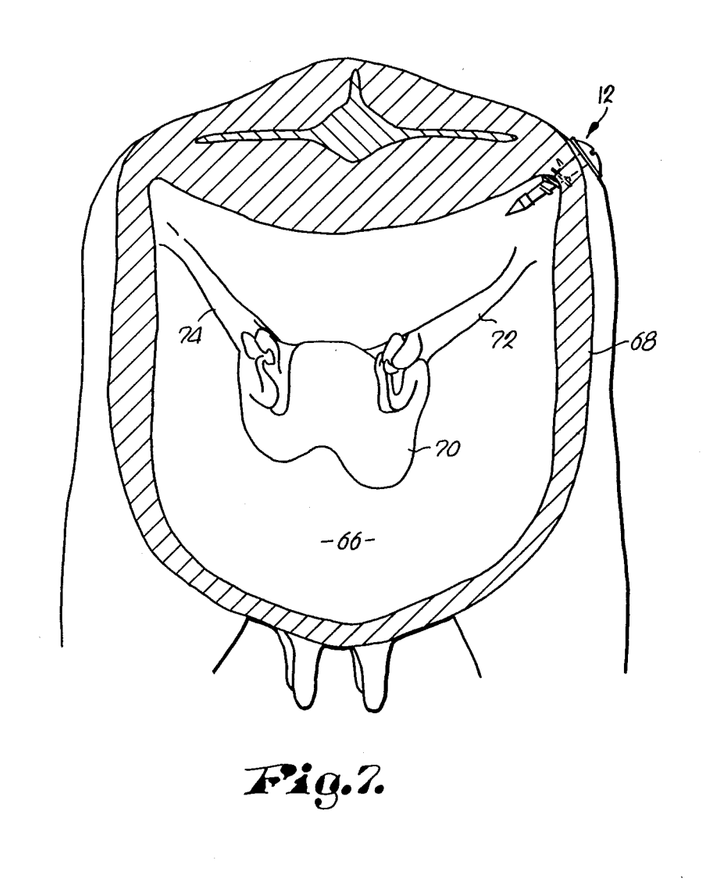
FIG. 7 is a schematic, sectional view illustrating the abdominal cavity of a cow, along with the cow's uterus, and with the valve assembly of the FIG. 1 embodiment inserted in place on the cow extending into the cow's body.
Figure 8:
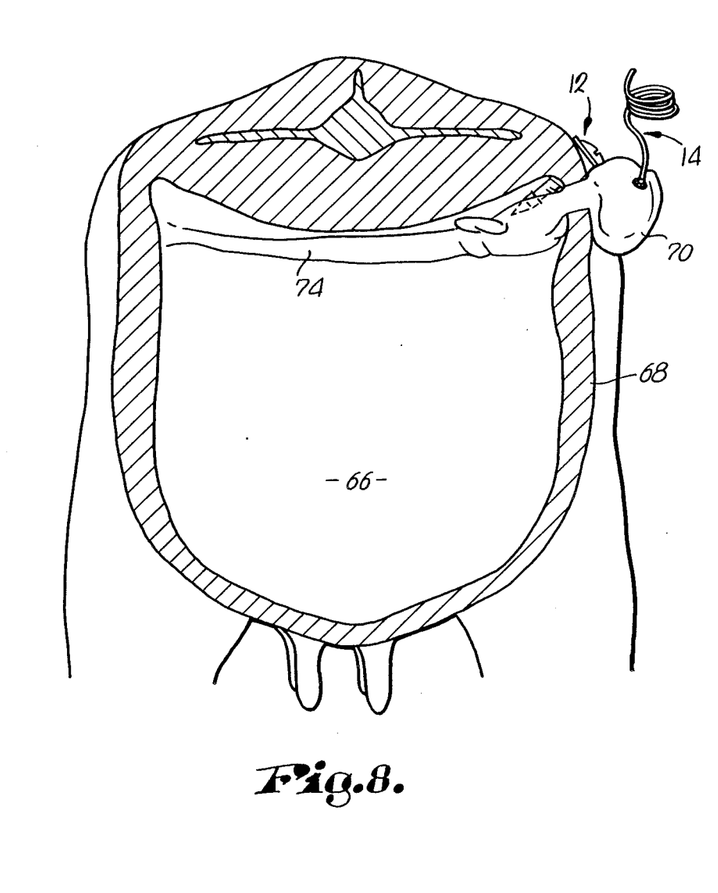
FIG. 8 is a view similar to that of FIG. 7 and illustrates the uterus removed with the inner end of the fluid-conveying conduit secured to the uterine wall.
Figure 9:
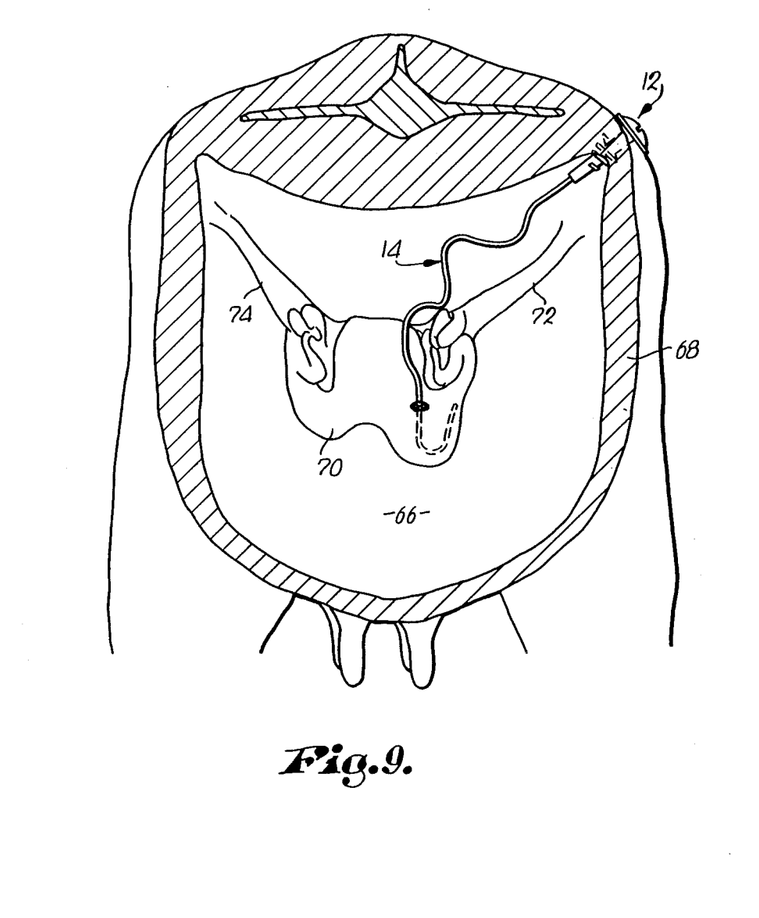
FIG. 9 is a view similar to that of FIG. 8, but illustrates the complete FIG. 1 apparatus in place.

The conduit 14 is advantageously in the form of plastic tubing which is dimensioned to receive and tightly engage the lower end of part 46 (see FIGS. 1 and 2), and thus be operatively connected to the tubular element 16. The end of conduit 14 remote from the valve assembly 12 is provided with a plurality of fluid flow apertures 62 through the defining wall thereof. In addition, an attachment collar 64 is situated on conduit 14 intermediate the ends thereof, and has an annular, outwardly extending cloth or synthetic resin attachment flange 65. As shown, this flange 66, is flexible and perforate and can be sutured to an organ wall; the flange should therefore extend at least about one-quarter of an inch outwardly from the conduit. The innermost portion of conduit 14 (i.e., the fenestrated portion below the flange 65) is adapted for insertion into the confines of the animal's organ. In FIGS. 7-9, the abdominal cavity 66 of a cow 68 is shown. The uterus 70, supported by ligaments 72, 74 is likewise depicted.

Installation of device 10 on cow 68 may involve initially tranquilizing the cow and administering a local anesthesia at the selected laparotomy site(s), typically left or right paralumbar fossa. A skin incision is next made, typically a caudal and dorsal to laparotomy incision. The valve assembly 12 is next inserted into the incision using a rotating action so that the component 20 is in effect screwed into and through the abdominal cavity wall until the inner end of the valve assembly is disposed within cavity 66 (see FIG. 7). Tack down sutures of non-absorbable suture material are next installed through the apertures 26 in head 24, in order to fixedly position the component 20, and thereby the element 16 and valving means 18 carried therein, on the cow 68.

The cow's uterus is next grasped and pulled outside of cavity 66 (see FIG. 8). If necessary, another incision is made in the abdominal cavity wall to permit such manipulation of the uterus. In any event, one may choose to make a small (1 cm.) incision through the uterine wall, and the fenestrated conduit 14 is inserted into the uterus; sufficient length is allowed within the uterus for uterine growth and descent into the abdominal cavity as gestation proceeds. That is to say, the length of conduit 14 is greater than the shortest distance between the element 16 and the point of insertion through the uterus; this construction along with the flexibility of the conduit, permits and accommodates natural movement of the uterus over time. A so-called "purse string" suture is then placed through the uterine wall and the flange 65, using suture material. The incision and suture are then checked for fluid leakage, and the collar 64 is further secured to conduit 14 by gluing. In this fashion, the inner end of conduit 14 is physically attached and interlocked with the uterine wall; and this effect is enhanced by virtue of the formations of adhesions around the suture site which occurs within a few days after device 10 is installed.

The uterus 70 is next replaced in its normal position, making certain that sufficient excess tubing is present to connect with the part 46 and allow for normal animal movement and fetal growth. The penetrating point or tip 60 is next removed, and the free end of conduit 14 is operatively coupled with the valve assembly 12 by passing the end of the conduit into component 20 and over part 46 (see FIG. 2). The caps 30 and 58 are then removed, and a syringe 76, with needle removed, is used to aspirate the apparatus and check for fluid flow. The caps 30, 58 are next replaced, and the laparotomy incision is closed.

In a typical procedure for the production of monoclonal antibodies, inoculation of the cow's uterus or fetus may occur 5-7 days after installation of apparatus 10, assuming that the cow's systemic inflammatory response has decreased and after it has been determined that the pregnancy is being maintained. Such inoculation would include introduction of conditioning reagents (e.g., pristane, albumins and the like) in uterine fluids, followed by inoculation of the cell lines. Incubation varies with the specific cell line selected, and in general the uterine fluids are monitored periodically using apparatus 10. When it is desired to harvest the cell line and its products, such may be accomplished through the use of device 10, through cesarean section, or by sacrificing the cow and obtaining the selected utrine fluids. Typical enrichment constituents added to the uterine fluid during the incubation sequence would include, amino acids, bovine serum albumin, vitamins, inorganic salts, and suspension mediums and growth factors. More specifically, amino acids such as L-Glutamine, L-Argine, L-Cystine, and L-Histadine $HCl.H_2O$ may be added. Vitamin addition may include D-Calcium Pantothenate, Thiamine HCl, Choline Chloride and Riboflavin. Inorganic salts may include KCl, $NaHCO_3$, $NaH_2PO_4.H_2O$, and $CaCL_2.2H_2O$. Finally, suspension mediums such as Dextrose, Phenol Red, $MgCl_2.6H_2O$, and NaCl, KCl may be included.

When it is desired to utilize apparatus 10 either for introduction of fluids into, or removal of fluids from, the cow's uterus, the following procedure obtains. First, the caps 30, 58 are removed, and a syringe 76 (see FIG. 2), with needle removed, is pressed downwardly into the upper end of member 38 until the actuator 56 is encountered. The syringe is thereupon pressed inwardly with the effect that the plug 50, and particularly surface 52 thereof, is shifted away from mating surface 42 against the bias of spring 54. When this occurs, it will be seen that a fluid flow path is established through tubular actuator 56, passage 40, the bore of part 46, and conduit 14. Thus, fluids can be administered through apparatus 10 into uterus 70 simply by manipulating syringe 76 in the usual injection manner. By the same token, fluids can be withdrawn from the uterus by the opposite manipulation of syringe 76, as those skilled in the art will readily appreciate.

It should also be understood that while the apparatus and method have been illustrated in connection with a cow's uterus, the invention is not so limited. For example, the apparatus can be used with virtually any large mammal such as sheep, goats or cattle. In addition, other body parts or organs can be connected to the apparatus hereof., e.g., the bladder, intestine or rumen compartments.

In this connection, it is particularly advantageous to employ pregnant hosts where the placenta acts as a barrier and will not allow maternal antibodies to cross into the uterine compartments. These types of placenta are sometimes referred to as epitheliochorial (found in animals such as horse, pig, cow and sheep) and syndesmochorical. These placenta provide a functional and imminological isolation of the fetus from the maternal immune system, and therefore use of pregnant hoss having these types of placenta is preferred.

Figures 10, 11, 12, 13:
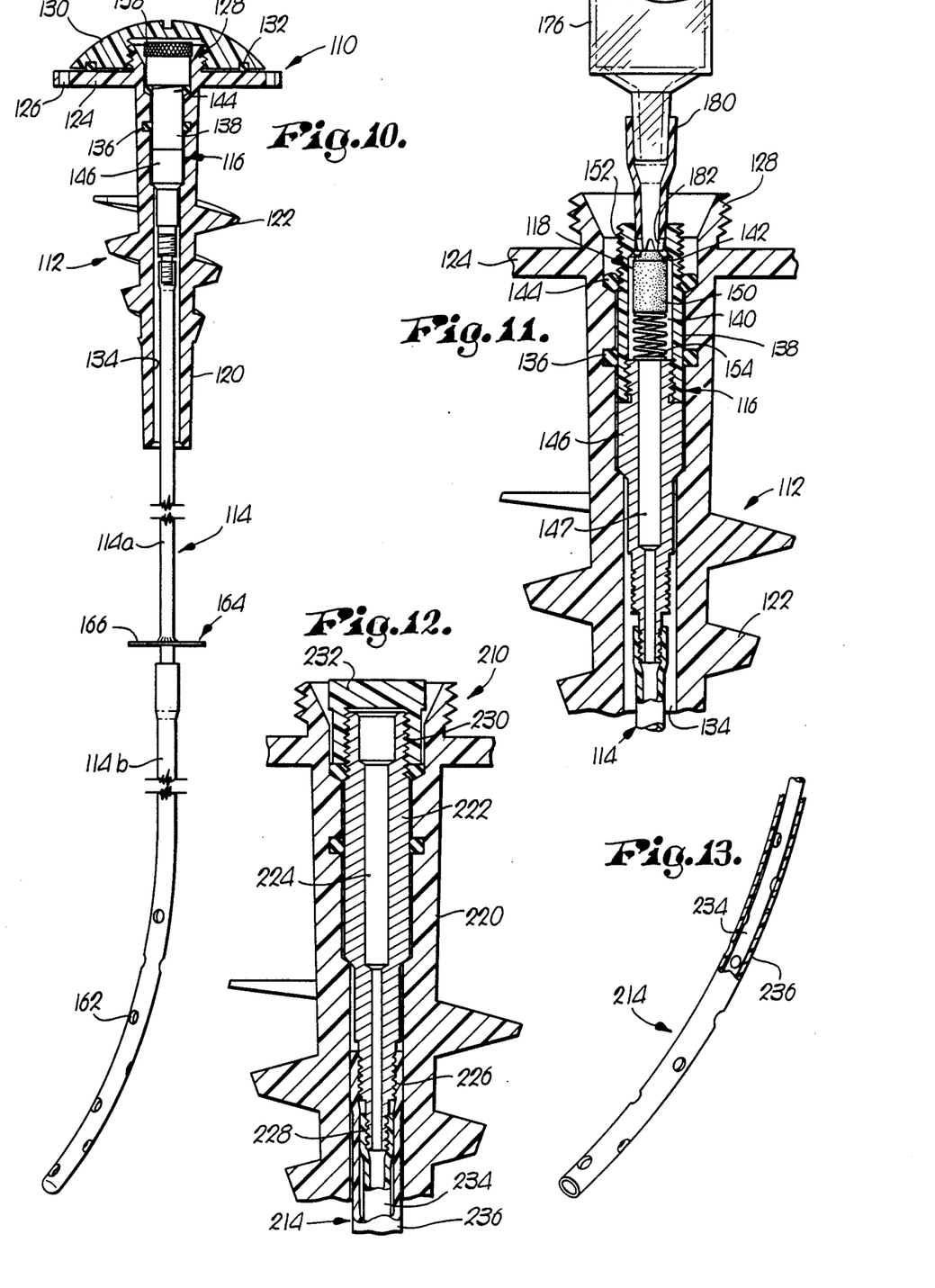
FIG. 10 is a view similar to that of FIG. 1 but illustrating another embodiment of the invention wherein use is made of a fluid-conveying conduit with the inner portion thereof having a diameter larger than that of the main portion of the conduit.
FIG. 11 is an enlarged, fragmentary view in partial vertical section illustrating the valve assembly of the FIG. 1 apparatus, with a syringe positioned for operating the internal valve.
FIG. 12 is a view similar to that of FIG. 11 but illustrating another embodiment which does not employ an internal, mechanical valve.
FIG. 13 is a fragmentary view in partial section depicting a fluid-conveying conduit for use in the invention wherein the conduit includes a pair of telescopically interfitted tubular members.

Turning now to FIGS. 10-11, a second embodiment of the apparatus is illustrated. In this instance fluid conveying apparatus 110 is provided which in many respects is identical to apparatus 10. Thus, the apparatus 110 includes a valve assembly 112 along with an elongated, flexible, fluid conveying conduit 114. The valve assembly 112 has an elongated, tubular, fluid-conveying element 116, as well as valving means 118 carried within the element 116.

The overall valve assembly 112 includes an elongated, tapered, tubular, externally threaded synthetic resin component 120 having a screw thread 122 and an enlarged flange-type head 124 having apertures 126 therethrough. The head 124 further includes an upstanding, central, threaded annular connector 128. Outermost cap 130 is threaded onto connector 128 as illustrated, and includes an O-ring seal 132 which abuts the upper surface of head 124. The component 120 presents a continuous, stepped internal bore 134 along the length thereof and has an internal O-ring seal 136 spaced downwardly from head 124.

The tubular element 116 is situated within bore 34 and includes an upper synthetic resin tubular member 138 which is threaded at its upper end, the latter extending to a point adjacent the surrounding connector 128 and having a removable cup 158. The inner surface of member 138 defines a fluid-conveying passage 140 (see FIG. 11) and presents an annular, obliquely oriented engagement surface 142 proximal to the upper end thereof. A secondary O-ring seal 144 is disposed about the upper end of member 138, and is situated within the upper end of bore 134.

The lowermost end of element 116 is internally threaded and receives a lowermost tubular part 146. The part 146 includes an internal bore 147, and extends along the length of bore 134 in substantially conforming relationship thereto. The lowermost end of part 146 is threaded (see FIG. 11), in order to facilitate secure attachment to the outer end of conduit 114 thereto.

Valving means 118 is situated to normally block the flow of fluid through the element 116. In detail, the valving means 118 includes a shiftable plug 150 presenting a conical upper sealing surface 152 which is complemental with and adjacent engagement surface 142. A spring 154 is situated between the underside of plug 150 and the uppermost annular surface of part 146, and serves to bias the plug 150 against surface 142 for purposes of normally sealing the member 138, and thus the overall tubular element 116, against fluid flow therethrough.

The conduit 14 is advantageously in the form of an outermost stretch of relatively small diameter synthetic resin tubing (e.g., Tygon) 114a which is secured to the part 146, along with an innermost end stretch 114b which is attached to the section 114a. The innermost portion 114b is designed to be inserted through the organ or the like of a host animal, and is advantageously of a somewhat larger diameter than the stretch 114a. The innermost portion 114b includes a series of openings 162 therethrough, and is advantageously formed from a soft, flexible material such as silicon rubber.

The overall length of the conduit 114 is sufficient to extend between the element 116 and the specific organ of the host animal, with added length to accommodate and permit natural movement of the organ.

The conduit 114 further includes an attachment collar 164 which is affixed to stretch 114 adjacent the innermost end thereof. The collar 164 includes an outwardly extending flexible flange 166 which can be physically attached, as by suturing and/or gluing, to the wall of the selected host organ.

Use of the two component conduit 114 is advantageous in that the relatively small diameter stretch 114a resists collapse under suction conditions, but has sufficient strength to accommodate organ movement without tearing. On the other hand, the enlarged diameter (up to about one-half inch) fenestrated portion 114b permits collection of fluid samples from the organ without clogging or the like.

The device 110 is installed in the same manner as heretofore described with respect to device 10.

During use of apparatus 110 either for introduction of fluids into, or removal of fluids from, a host organ, the caps 130, 158 are removed, and a syringe 176, with needle removed, is provided. A separate, removable, synthetic resin tubular tip 180 is provided having a lowermost, notched plug-engaging end 182 and is affixed to the delivery end of flange 176. The flange and tip are then pressed downwardly into the upper end of member 138 (see FIG. 11) in order to shift the plug, and particularly surface 152 thereof, away from mating surface 142 against the bias of spring 154. When this occurs, a fluid flow path is established through conduit 114, element 116, tip 180 and syringe 176. Thus, fluids can be administered through apparatus into an organ simply by manipulating syringe 176 in the usual injection manner. By the same token, fluids can be withdrawn by the opposite manipulation of syringe 176.

While the apparatus depicted in FIGS. 1-6, and in FIGS. 10-11, include a selectively openable valve assembly 18, 118, the invention is not so limited. For example, and referring to FIG. 12, an apparatus 210 is depicted. This apparatus includes an outer tubular component 220 identical to the component 120, along with a tubular, capped insert 222. The insert 222 includes an elongated stepped bore 224 along the length thereof, and is provided with a pair of threaded regions 226, 228 adjacent the lower end thereof. The component 222 has a threaded uppermost end 230 and a removable cap 232. The overall apparatus 210 includes a flexible conduit 214 having overall length and flexibility properties similar to the conduits 14, 114 described above. However, in this instance a pair of telescopically interfitted tubular members 234, 236 are employed, with the innermost 234 being frictionally secured to the threaded region 228, while the outer member 236 is frictionally coupled to the threaded region 226 (see FIG. 12). Use of a pair of telescopically interfitted members can be advantageous, particularly inasmuch as this construction resists crimping and resultant fluid blockage during normal movement of the host and/or the selected organ. The innermost end of the conduit 214 is fenestrated (see FIG. 13), and includes an attachment collar (not shown). Installation of device 210 involves the identical steps depicted and described above.

In the use of apparatus 210, the cap 232 is removed, and a syringe is employed to inject fluid into, or withdraw fluids from, the host's organ. However, as mentioned above, this embodiment of the invention does not include a separate valving unit.

As noted above, the apparatus and method of the invention are particularly adapted for use in large-scale in vivo production of monoclonal antibodies. To this end, it has been discovered that the cell line to be employed should be initially educated to the anticipated in vivo environment. Such education generally refers to an adjustment of the growth and metabolism characteristics of the cells to the new environment, and is generally accomplished by an in vitro contact of the cells with the ambient fluid to be experienced in the animal host, followed by inoculation of the educated cells.

In practice, the cell education technique normally involves repeated or stepwise contact of the cells with respective, increasing quantities of the ambient fluid over a period of time, typically as long as several days to several weeks. The ambient fluid can be derived from the host itself, or more usually from the same type of animal as the host.

In particularly preferred forms, the host animal is a pregnant cow, and the ambient fluid is either the allantoic or amniotic fluid of the cow's uterus, with the allantoic fluid being the most preferred for reasons hereinafter described. In this case, the cells are contacted with a mixture of various nutrients and the appropriate uterine fluid, until cell acclimation is established by the appropriate in vitro growth rate. During such in vitro cell education, the cells are advantageously maintained at a temperature of from about 38.3-39.0 degrees centigrade. In addition, the cells are initially contacted with a fluid containing from about 5 to 10 percent by volume of the ambient fluid, followed by cultivation and incubation therein. Thereafter, the cells may be contacted with a fluid in increasing concentrations to achieve optimal growth and education.

In practice, this portion of the technique is carried out to accomplish the following goals:

1. To determine if the particular cell line in question encounters any toxic effects due to some unknown factor in the ambient fluid. Such would be indicated by immediate death or eventual starvation because of some nutrient deficiency;
2. The concentration of ambient fluid at which slowing or cessation of cell growth may occur. This is determined by adding the ambient (e.g., uterine) fluid to normal in vitro culture fluid in a stepwise manner of increasing concentrations, 5%, 10% ... 100%. At each concentration level cell line kinetics are measured, and growth rates and the continued ability-to produce antibody are determined. At some level. (e.g., 50% ambient fluid/50% culture media) the cells may slow their growth rate to an unacceptable level and/or "shut-off" producing the desired antibody. Should one or both of the above occur, then the environment in vivo should be manipulated to stay within the parameters of optimal cell growth. This may be done by enrichment with additional nutrients (e.g., 20% by volume fetal calf serum), growth factors (chemical or biological i.e., fibroblasts, macrophages), or maintenance of proper volume concentration, such as e.g., 45% ambient fluid/55% culture media. Completion of these steps may take several days to several weeks depending on the cell line and the technician.

As noted above, it has heretofore been suggested that large scale production of monoclonal antibodies could be effected in the amniotic fluid of a pregnant mammal such as a cow, providing such was accomplished prior to the onset of immunocompetency of the fetus. However, this approach has led to a number of problems. It has now been discovered that a greatly improved method of cell growth can be provided through use of the allantoic uterine fluid, as compared with the amnionic fluid. Use of this fluid medium offers a number of practical advantages. First, the allantoic fluid is more dynamically stable over time in that the allantoic fluid maintains its fluid consistency throughout the gestation period, and does not convert into a gel-like substance which is detrimental to cell growth and presents serious practical problems from the standpoint of harvesting. In the case of bovine allantoic fluid, there is a steady increase in volume thereof throughout gestation, to an average volume of 6 to 9 liters, whereas bovine amnionic fluid increases in volume up to a gestational age of approximately 160 days, and then decreases (average max. volume of 3.5 l in the bovine).

In addition, cells located in allantoic fluid are selectively isolated from both maternal and fetal immune response. Hence, the "antigen" represented by a hybridoma cell line inoculated into the allantoic sac is effectively separated from the fetus, and the fetus does not ingest the allantoic fluid as in the case of amnionic fluid. Should "leakage" occur from the allantoic to the amnionic sac, allowing an immunocompetent fetus to produce antibody against the hybridoma, it is believed that any antibody so produced is not secreted or excreted by the fetus into the allantoic fluid. Inasmuch as the amnionic sac and allantoic sac are separate compartments within the uterus, bacterial contamination will be isolated from fetal swallowing when contained in the allantoic sac. Therefore, if infections are detected early enough, they can be treated with appropriate antibiotics before fetal infection occurs, providing an opportunity to maintain the pregnancy.

Use of the allantoic sac also provides a number of surgical advantages. For example, in later gestational ages (second-third trimester) when allantoic fluid volumes begin to surpass those of the amnionic fluid, there are resulting anatomical changes in the position of the uterus in the peritoneal cavity of the animal, particularly in the case of the cow. Accordingly, this anatomical repositioning allows surgical access to the uterus via flank approaches or ventral abdominal approaches. In contrast, one wishing to use the amnionic fluid during the "fluid phase" (basically the first trimester) must employ flank incisions because ventral abdominal approaches are not practical. In addition, the fetus can be manipulated by the surgeon during older gestational ages (6-9 months) with less danger of inducing a spontaneous abortion. Such fetal manipulation during the first trimester of gestation in the bovine generally results in a high incidence of spontaneous abortion. Finally, in the 6-9 month gestational age, for instance, it is easy to distinguish between the yellow fluid consistency of the allantoic fluid and the clear, contrastingly high viscosity content of the amnionic sac. This makes an easy "landmark" for the surgeon.

In terms of the nutritional qualities of allantoic fluid, such are comparable to amnionic fluid in many areas. For example, bovine allantoic fluid has a greater content of fructose, total protein and free fatty acid, as compared to amnionic fluid, and has somewhat less, though significant, amounts of glucose.

For all of the foregoing reasons, then, the allantoic fluid provides a more ideal environment for cell growth, particularly in the context of production of monoclonal antibodies. This is especially true when cell growth occurs after the onset of immunocompetency of the host fetus, something which is precluded by prior methods seeking to employ amnionic fluid.

EXAMPLES

The following examples described techniques in accordance with the invention. It is to be understood, however, that nothing in the examples should be taken as a limitation on the overall scope of the invention. Rather, the examples are for illustrative purposes only, in order to elucidate the principles of the invention.

Example I

This examples sets forth a procedure for the in vitro education of hybridoma cells. The materials employed were:

| POI-STOCK | |
|---|---|
| Oxalacetic acid | 660 mg. |
| Pyruvate | 250 mg. |
| Distilled $H_2O$ | 50 ml. |
| Insulin | 40 mg. |

The above materials are slightly heated while stirring, and are aliquoted and frozen.

| HT-Stock | |
|---|---|
| Hypoxanthine | 136 mg. |
| Thymidine | 38.8 mg. |
| Distilled $H_2O$ | 100 ml. |

The above materials are mixed, aliquoted and frozen.

| H-T Medium | |
|---|---|
| RPMI | 325 ml. |
| NCTC-135 | 50 ml. |
| Fetal Calf Serum (FCS) | 100 ML. |
| POI-Stock | 5 ml. |
| HT-Stock | 5 ml |
| L-Glutamin | 5 ml. |
| Pen/Strep | 5 ml. |
| Non-essential Amino Acids | 5 ml. |

The RPMI medium is commercially available (e.g., Flow Laboratories, Cat. No. 12-603) and contains inorganic salts, amino acids, vitamins and other components. Similarly, the NCTC-135 medium is available from Catalog No. 44-1100 (1980) of Gibco Laboratories, 519 Aldo Avenue, Santa Clara, Calif. 95050. The components of the NCTC-135 medium are: inorganic salts (e.g., $CaCl_2$), amino acids (e.g., glycine), vitamins (e.g., niacin), co-enzymes (e.g., FAD, flavin, adenine, dinucleotide), reducing agent (e.g., ascorbic acid), nucleic acid derivative (e.g., thymidine) and additional components (e.g., d-glucose).

The Pen/Strep is a mixture of penicillin and streptomycin, and is available from a number of sources, including the Pfizer Chemical Co. The product contains 5,000 I.U./ml. penicillin and 5000 mcg./ml. streptomycin.

Amniotic Fluid

Obtained from cattle slaughterhouse from pregnant cow at not more than 80 days gestation. The fluid is filtered through Seitz filters (several steps) beginning with a pore size of 1.0 m, and decreasing pore size in stages (0.5, 0.2 and 0.1 mm). The filtered fluid is then heated to 56 degrees centigrade for 30 minutes. The fluid may then be tested for bovine virus diarrhea, bluetongue, leptospirosis, mycoplasma, or any other agents deemed necessary by the investigation laboratory, for example BVD, lepto, bluetongue, the presence of endotoxin, bacteria, etc.

Heat Inactivated FCS

FCS is heated to 56 degrees C. for 30 minutes, and is filtered before use using staged Seitz filters having pore sizes of 0.5 and 0.1 m.

In a specific cell education procedure, the cells (produced by fusion of NS-1 myeloma cells with mouse spleen cells immunized against IBR in cattle) were initially cultured at 38.3–39 degrees centigrade in H-T medium to a density of $10^5$ cells/ml. Ten percent heat inactivated FCS and five percent amniotic fluid were then added, and the mixture was allowed to incubate at 38.3–39 degrees centigrade for 48 hours. At the end of this period, another 5% amniotic fluid was added, and incubation was allowed to continue at the noted temperature.

When the cells grew to a density of $10^6$ cells/ml., the cells were split 1:3 using H-T medium with ten percent heat inactivated FCS and twenty percent amniotic fluid. The cells were then allowed to grow to $10^6$ cells/ml. density at 38.3–39 degrees centigrade, and were again split using the same procedure but with thirty percent amniotic fluid. Finally, all of the resultant cell colonies were grown to a density of $10^6$ cells/ml., and were checked for antibody production.

The entire cell education procedure took four days.

Example II

In this in vitro test, hybridoma cells as used in Example 1 were employed.

In a control, the cells were removed from their standard media and placed in uterine fluids (amniotic and allantoic). A death rate of 90-100 percent occurred within 24 hours of incubation at 39 degrees centigrade. No cells were found alive or producing antibody after 72 hours.

In a second test, the protocol above was generally followed except that the cells and their standard culture media (RPMI) was added to the uterine fluids (resultant media was 70 percent RPMI, 30 percent uterine fluid). The initial death rate was decreased to 60 percent after 24 hours of incubation at 39 degrees centigrade. The cells continued to multiply in vitro with the 70 percent RPMI/30 percent uterine fluid media during standard hybridoma culture and feeding techniques.

The second test was repeated except that FCS was added stepwise in various concentrations (5%; 10%; 15%; and 20%). These combinations were successful in lowering the initial death rate to 45-50 percent under standard in vitro culture methods at 39 degrees centigrade. Over several weeks of culturing, the proportion of RPMI was gradually reduced to less than 10 percent. At this point the hybridomas were educated, and were placed in the appropriate (90% amnionic fluid/10% FCS) uterine fluids (in vitro) for multiplication.

Next the cells were fed 10 percent FCS by volume every forty-eight hours for six feedings. At this point the cells continued to grow (multiply) at their normal rate plus maintained their antibody production level, even though subsequent feedings were discontinued. The first decline in multiplication rate was observed twelve days after the last feeding. Normally, hybridomas must be fed every forty-eight hours; however, the described education to the amnionic fluid allowed this time period to be extended.

Example III

This example gives a procedure for the education of myeloma or hybridoma cells prior to inoculation into the amniotic fluid of a pregnant cow.

Materials

1. Allantoic Fluid

Obtained from cattle slaughterhouse from pregnant cows at 3-9 months gestation. The fluid is clarified by low speed centrifugation and sterilized by filtration successively through a series of filters from 1.0 m down to 0.2 m. Endotoxin-free samples of fluid are pooled for use in tissue culture.

| Media | |
|---|---|
| Dulbecco's Minimal Essential Medium | 40–75% |
| Fetal calf serum | 20 |
| Pen/Strep, 10,000 units/ 10,000 mcg | 1 |
| Nutrient supplement[1] | 4 |
| Allantoic fluid | 0–40 |

[1]Nutrient supplement
L-glutamine, 200, mM, 100X
MEM Amino Acids, 100X
MEM Non-essential Amino Acids, 100X
Vitamins, 100X

Method

In a control test, myeloma cells capable of producing antibody against surface antigens of pneumococcus organism were placed in allantoic fluid and tested for survival over a period of 72 hours. A death rate of 50% occurred in 24 hours and at 72 hours 10 percent of the cells were viable.

These myeloma cells were used in an in vitro education test to allantoic fluid. Cells were seeded at $5 \times 10^5$/ml in complete medium. Subsequent passage was set up with the media supplemented by 10% every 48 hours during feeding, up to a maximum level 4 percent allantoic fluid. During this test the growth rate of the myeloma cells remained steady up to the 40 percent allantoic fluid level.

Example IV

The cell line chosen for this study was the murine BALB/C myeloma MOPC 315J which constitutively produces a monoclonal IGA molecule having binding specificity for the trinitrophenol group (TNP). 315J cells are grown in Dulbecco's minimal essential medium supplemented with 20 percent fetal calf serum, antibiotics and a nutrient cocktail consisting of L-glutamine, MEM amino acids, MEM non-essential amino acids, sodium pyruvate, and vitamins. Supernatants of 315J cells grown for a period of time routinely contain up to 1 microgram/ml IgA as measured by radio-immunoassay (RIA). Cultures are routinely grown from $5\times10^5$ cells/ml to a concentration $2-5\times10^6$ cells per ml. with refeeding every 2 days. Frozen stocks are maintained at $-70$ degrees centigrade or in liquid nitrogen.

The antibody production by 315 J cells is routinely measured by RIA or any enzyme-linked immunoadsorbant assay (ELISA). These assays will quantitate the concentration of antibody in either culture fluids or uterine fluids. The rosette assay will identify and quantitate the number of 315J myeloma cells in culture or from uterine fluids. This assay involves attaching the binding antigen (TNP) to sheep red blood cells. Using these assays (RIA, ELISA AND Rosette) both myeloma (hybridoma) cells and their products, monoclonal antibodies, can be identified and quantitated.

Respective colonies of cells were placed in allantoic fluid, in the usual complete medium, and in balanced salt solution and incubated in vitro. Tests were made for cell survival over a period of 72 hours. A death rate of fifty percent occurred in 24 hours and at 72 hours 10 percent of the myeloma cells were viable when they were in allantoic fluid. On the other hand, the cells in balanced salt solution died at a faster rate, 50 percent in 6 hours and 100 percent in 20 hours. Myeloma cells cultured in complete media doubled in number by 24 hours. These results demonstrated that the allantoic fluid is not toxic but does not have enough nutrients to induce these cells to divide.

The next step was to educate the myeloma cells to grow in medium containing allantoic fluid. Cells were seeded at $5\times10^5$/ml in complete medium. Subsequent passage was set up with the media supplemented with 10 percent allantoic fluid. The percentage of allantoic fluid was increased by 10 percent with every 48 hours feeding up to 40 percent allantoic fluid. By this method the growth rate of the myeloma cells remained steady.

Myeloma cells, both educated and uneducated, were then injected in the allantoic fluid of pregnant sheep at approximately 100 days gestation, after the onset of fetal immunocompetency. The device employed for the cell inoculation and subsequent fluid withdrawals was of the type illustrated in FIGS. 10–11, and the device was installed in the manner described previously, where the inner end of the fluid conduit was affixed to the allantoic sac of the sheep. Pathological samples of tissue from the sheep indicated that myeloma-like cells are found in groups in the placental tissue in cases of both educated and uneducated myeloma cell injection.

Cells taken from samples of sheep allantoic fluid were also counted with time after injection. In one example, $10^8$ uneducated myeloma cells were injected into a sheep with 500 ml. allantoic fluid (estimated). Ten ml. samples were removed daily for 7 days. Beginning with day 1, $8.5\times10^7$ cells were estimated to be in the allantoic fluid. Cell numbers decreased daily but by 7 days $2.5\times10^7$ cells were still present. This is a tremendous number of cells to be left when the cells injected were uneducated and no nutrients were added for their growth.

I claim:

1. A method of in vitro cell culturing comprising contacting cells to be cultured with a medium including a quantity of allantoic fluid derived from a pregnant animal having a placenta, and a quantity of serum added to the allantoic fluid which is not otherwise present in the allantoic fluid, and allowing said cells to culture in said medium.

2. The method of claim 1 wherein said animal is selected from the group consisting of sheep, horses, cows and pigs.

3. The method of claim 1, said cells being hybridoma cells.

4. The method of claim 1, said allantoic fluid being admixed with fetal calf serum.

5. A culture medium for in vitro culturing of cells and further comprising a quantity of allantoic fluid derived from a pregnant animal having a placenta, admixed with an amount of serum which is not otherwise present in said allantoic fluid.

6. A culture medium for in vitro cell culturing comprising a quantity of uterine fluid derived from a pregnant animal admixed with an amount of serum not otherwise present in said allantoic fluid, the uterine fluid present in said medium consisting essentially of allantoic fluid.

* * * * *